United States Patent [19]

Mooradian

[11] 3,931,223

[45] Jan. 6, 1976

[54] 3-(DIMETHYLAMINO)-1,2,3,4,8,9-HEXAHYDRO-1H[1]BENZAZEPINO[1,2,3-K,J]CARBAZOLE

[75] Inventor: Aram Mooradian, Schodack, N.Y.

[73] Assignee: Sterling Drug Inc., New York, N.Y.

[22] Filed: June 3, 1974

[21] Appl. No.: 475,446

[52] U.S. Cl.......... 260/315; 260/239 D; 260/563 C; 424/274
[51] Int. Cl.² ..................................... C07D 209/88
[58] Field of Search .................................... 260/315

[56] References Cited
UNITED STATES PATENTS
3,592,824  7/1971  Schut................................. 260/315

OTHER PUBLICATIONS

J. Chem. Soc., Perkin Trans. 1, (1973), pp. 1041–1047, Cattanach et al.

*Primary Examiner*—Sherman D. Winters
*Attorney, Agent, or Firm*—Frederik W. Stonner; B. Woodrow Wyatt

[57]  ABSTRACT 3-(Dimethylamino)-1,2,3,4,8,9-hexahydro-1H[1]benzazepino[1,2,3-k,j]carbazole and acid-addition salts thereof having anti-bacterial activity, and process for the preparation thereof are disclosed.

3 Claims, No Drawings

3-(DIMETHYLAMINO)-1,2,3,4,8,9-HEXAHYDRO-1H[1]BENZAZEPINO[1,2,3-K,J]CARBAZOLE

The invention sought to be patented resides in the chemical compounds designated as 3-(dimethylamino)1,2,3,4,8,9-hexahydro-1H[1]benzazepino[1,2,3-k,j]carbazole having the formula:

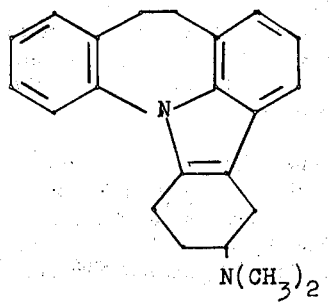

and acid-addition salts thereof.

The compound of the invention having formula I and acid-addition salts thereof exhibit antibacterial activity as more fully described hereinbelow.

The compound of formula I is prepared by the Fischer indole synthesis. Thus, the compound is prepared by reacting 4-dimethylaminocyclohexanone with 5-amino-10,11-dihydro-5H-dibenz[b,f]azepine in a suitable solvent in the presence of an acidic agent. The acidic agent should be present in at least one mole excess per mole of the aminodibenzazepine.

The compound of formula I, by virtue of possessing an asymmetric carbon atom at the 3-position, that is, the position at which the 3-dimethylamino group occurs, can exist as optical isomers. Therefore, within the purview of the invention are the dextrorotatory isomer and levorotatory isomer and the racemic mixture of the compound of formula I. The racemic mixture may be separated into the d-isomer and l-isomer using standard resolution procedures.

The compound of the invention having formula I is useful both in the free base form and in the form of acid-addition salts, and both forms are within the purview of the invention. The acid-addition salts are simply a more convenient form for use, and in practice, use of the salt form inherently amounts to use of the base form. When the compound of the invention having formula I is to be utilized for pharmaceutical purposes, the acids which can be used to prepare the acid-addition salts include preferably those which produce, when combined with the free base, medicinally acceptable salts, that is, salts whose anions are relatively innocuous to the animal organism in medicinal doses of the salts, so that the beneficial properties inherent in the free base are not vitiated by side effects ascribable to the anions. Appropriate medicinally acceptable salts within the scope of the invention are those derived from mineral acids such as hydrochloric acid, hydrobromic acid, hydriodic acid, nitric acid, phosphoric acid, sulfamic acid, and sulfuric acid; and organic acids such as acetic acid, citric acid, tartaric acid, lactic acid, cyclohexanesulfamic acid, methanesulfonic acid, ethanesulfonic acid, benzenesulfonic acid, p-toluenesulfonic acid, quinic acid, and the like, giving the hydrochloride, hydrobromide, hydriodide, nitrate, phosphate, sulfamate, acetate, citrate, tartrate, lactate, cyclohexanesulfamate, methanesulfonate, ethanesulfonate, benzenesulfonate, p-toluenesulfonate and quinate respectively.

The acid-addition salts of said basic compound are prepared either by dissolving the free base in aqueous or aqueous-alcohol solution containing the appropriate acid and isolating the salt by evaporating the solution, or by reacting the free base and acid in an organic solvent, in which case the salt separates directly or can be obtained by concentration of the solution or dilution of the solution with a solvent in which the salt is insoluble or only slightly soluble.

Although medicinally acceptable salts of said basic compound are preferred for pharmaceutical purposes, all acid-addition salts are within the scope of the invention. All acid-addition salts are useful as sources of the free base form even if the particular salt per se is desired only as an intermediate product as for example when the salt is formed only for purposes of purification or identification or when it is used as an intermediate in preparing a medicinally acceptable salt by ion exchange procedures.

The compound of formula I and acid-addition salts thereof possess useful antibacterial activity, thus indicating the utility of the compound of formula I and acid-addition salts thereof as antibacterial agents.

The antibacterial activity was determined using a modification of the Autotiter method described by Goss et al., Applied Microbiology 16 (No. 9), 1414–1416 (1968) in which a 1000 mcg./ml. solution of the test compound is prepared. To the first cup of the Autotray is added 0.1 ml. of the test solution. Activation of the Autotiter initiates a sequence of operations by which 0.05 ml. of the test compound solution is withdrawn from this cup by a Microtiter transfer loop and diluted in 0.05 ml. of sterile semi-synthetic medium (glucose). After this operation, 0.05 ml. of inoculated semi-synthetic medium is added automatically to each cup. The overall operation results in final drug concentrations ranging from 500 to 0.06 mcg./ml. in twofold decrements. The Autotray is incubated for 18–20 hours at 37°C., at which time the trays are examined visually for growth as evidenced by turbidity, and the concentration of the last sample in the series showing no growth (or no turbidity) is recorded as the minimal inhibitory concentration (MIC).

The compound of formula I and its hydrochoride salt were found to be antibacterially effective against *Staphylococcus aureus* at a concentration of 15.6 mcg./ml.

The actual determination of the numerical biological data definitive for a particular compound is readily determined by standard test procedures by technicians having ordinary skill in pharmacological test procedures, without the need for any extensive experimentation.

The compounds of the invention can be formulated for use by preparing a dilute solution in an aqueous medium or in a solution containing a surfactant, or alternatively in an organic medium in which the compounds are soluble, for example ethyl alcohol, and are applied to a surface to be disinfected by conventional means such as spraying, swabbing, immersion, and the like. Alternatively, the compounds can be formulated as ointments or creams by incorporating them in conventional ointment or cream bases, for example alkylpolyether alcohols, cetyl alcohol, stearyl alcohol, and the like, or as jellies by incorporating them in conventional jelly bases as glycerol and tragacanth. They can also be formulated for use as aerosol sprays or foams.

The molecular structure of the compound of the invention having formula I was assigned on the basis of the method of its synthesis and study of its infrared and nuclear magnetic resonance spectra, and confirmed by the correspondence between calculated and found values for the elementary analysis.

The invention is illustrated by the following example without, however, being limited thereto.

EXAMPLE 1

A solution of 5-amino-10,11-dihydro-5H-dibenz[b,f]azepine hydrochloride (24.7g.) and 4-dimethylaminocyclohexanone (14.1g) in absolute ethyl alcohol (100 ml.) was heated at reflux for one-half hour. Alcoholic hydrogen chloride (6-N; 75 ml.) was added cautiously in small portions. Heating was continued at reflux for one-half hour and the reaction mixture was cooled. The precipitate was collected by filtration, washed with water and isopropyl alcohol and recrystallized from methanol-isopropyl alcohol (2:1) to give 3-(dimethylamino)-1,2,3,4,8,9-hexahydro-1H[1]benzazepino [1,2,3-k,j]carbazole hydrochloride (17.1g.), m.p. 300°–303°C.

A suspension of the above hydrochloride salt in water was treated with ammonium hydroxide and the aqueous mixture was extracted with chloroform. The chloroform extract was evaporated to dryness and the resulting residue was crystallized from isopropyl alcohol-water to yield 3-(dimethylamino)-1,2,3,4,8,9-hexahydro-1H[1]benzazepino [1,2,3-k,j]carbazole (76% yield), m.p. 85°–88°C.

The base thus obtained can be converted to any desired acid-addition salt, for example, hydrobromide, sulfamate, tartrate, lactate and the like in the manner hereinabove described.

I claim:
1. 3-(Dimethylamino)-1,2,3,4,8,9-hexahydro-1H[1]benzazepino[1,2,3-k,j]carbazole or a medicinally acceptable acid-addition salt thereof.
2. 3-(Dimethylamino)-1,2,3,4,8,9-hexahydro-1H[1]benzazepino[1,2,3-k,j]carbazole according to claim 1.
3. 3-(Dimethylamino)-1,2,3,4,8,9-hexahydro-1H[1]benzazepino[1,2,3-k,j]carbazole hydrochloride according to claim 1.

* * * * *